(12) United States Patent
Feng et al.

(10) Patent No.: US 10,192,677 B2
(45) Date of Patent: Jan. 29, 2019

(54) METHOD AND APPARATUS FOR LEAKAGE MONITORING FOR OIL-IMMERSED ELECTRICAL TRANSFORMERS

(71) Applicant: ABB Inc., Cary, NC (US)

(72) Inventors: Xianyong Feng, Cary, NC (US); Mirrasoul Mousavi, Cary, NC (US)

(73) Assignee: ABB Inc., Cary, NC (US)

( * ) Notice: Subject to any disclaimer, the term of this patent is extended or adjusted under 35 U.S.C. 154(b) by 730 days.

(21) Appl. No.: 14/457,768

(22) Filed: Aug. 12, 2014

(65) Prior Publication Data

US 2016/0047765 A1    Feb. 18, 2016

(51) Int. Cl.
| | |
|---|---|
| *G01N 25/72* | (2006.01) |
| *H01F 27/40* | (2006.01) |
| *G01M 3/00* | (2006.01) |
| *G01N 25/18* | (2006.01) |

(52) U.S. Cl.
CPC .......... *H01F 27/402* (2013.01); *G01M 3/002* (2013.01); *G01N 25/18* (2013.01); *G01N 25/72* (2013.01); *H01F 2027/406* (2013.01)

(58) Field of Classification Search
CPC .... G01M 3/002; H01F 27/402; H01F 27/404; H01F 2027/406; G01N 25/72; G01N 25/18
USPC ......................................................... 702/183
See application file for complete search history.

(56) References Cited

U.S. PATENT DOCUMENTS

| | | | |
|---|---|---|---|
| 5,798,452 A * | 8/1998 | Martin ................... | G01N 9/002 73/32 R |
| 6,962,435 B2 | 11/2005 | Stenestam | |
| 7,089,145 B2 | 8/2006 | Stenestam et al. | |
| 7,145,760 B2 | 12/2006 | Stenestam et al. | |
| 7,444,266 B2 | 10/2008 | Stenestam et al. | |
| 8,260,472 B2 | 9/2012 | Hoffman et al. | |
| 9,419,430 B1 * | 8/2016 | Tostrud .............. | G06Q 10/0635 |
| 2005/0223782 A1 | 10/2005 | Dohi et al. | |
| 2009/0180514 A1 | 7/2009 | Anderson | |

(Continued)

FOREIGN PATENT DOCUMENTS

WO      2009005810 A1    1/2009

OTHER PUBLICATIONS

Radakovic et al, New Method for the Calculation of the Hot-Spot Temperature in Power Transformers With ONAN Cooling, ieee, 2003.*

(Continued)

*Primary Examiner* — Gregory J Toatley, Jr.
*Assistant Examiner* — Lynda Dinh
(74) *Attorney, Agent, or Firm* — Taft Stettinius & Hollister LLP; J. Bruce Schelkopf

(57) ABSTRACT

The present invention comprises an apparatus and method for detecting a loss of oil from an oil-immersed transformer, based on fitting a transformer top-oil temperature model to online measurements in an iterative optimization process that yields fitted values for a first model parameter representing the top-oil temperature rise over ambient temperature and a second model parameter representing the oil time constant. Among the several advantages seen in the contemplated apparatus and method is the reduction in required instrumentation, whereby transformer oil leaks are indirectly detected without requiring pressure sensors or mechanical floats, although the presence of such sensors is not excluded by the teachings herein.

22 Claims, 6 Drawing Sheets

(56) References Cited

U.S. PATENT DOCUMENTS

2011/0156918 A1 6/2011 Santos
2013/0158897 A1* 6/2013 Jain .................. G01R 31/027
　　　　　　　　　　　　　　　　　　　　702/42

OTHER PUBLICATIONS

Gouda et al; Predicting transformer temperature rise and loss of life in the presence of harmonic load currents, 2011.*
Kane, Claude, ""Waterboarding Your Transformer"—How to Obtain the Secrets Your Transformer is Keeping", Technical Paper, available online at: http://www.dynamicratings.com/US/Application/Transformers/Technical%20Papers/TP9.pdf, publication date unknown, pp. 1-11.
Nordman, Hasse et al., "Temperature Responses to Step Changes in the Load Current of Power Transformers", IEEE Transactions on Power Delivery, vol. 18, No. 4, Oct. 2003, pp. 1110-1117.
Solteiro, Inocencio, "Transformer Monitoring System TEC System", ABB PPTR/AT, available online at: http://www02.abb.com/global/clabb/clabb151.nsf/0/bf8bee50e508756bc1257b9d004cd326/$file/1+Inocencio+Solteiro+-+Transformer+++Monitoring+System,+TEC+System.pdf, Jun. 5, 2013, pp. 1-42.
Susa, Dejan, "Dynamic Thermal Modelling of Power Transformers", Doctoral Dissertation, , TKK Dissertations 9, Helsinki University of Technology, Department of Electrical and Communications Engineering, Power Systems and High Voltage Engineering, Espoo, Finland, 2005, pp. 1-131.
Susa, Dejan et al., "Dynamic Thermal Modelling of Power Transformers", IEEE Transactions on Power Delivery, vol. 20, No. 1, Jan. 2005, pp. 1-8.
Swift, Glenn et al., "A Fundamental Approach to Transformer Thermal Modeling—Part I: Theory and Equivalent Circuit", IEEE Transactions on Power Delivery, vol. 16, No. 2, Apr. 2001, pp. 1-5.
Swift, Glenn et al., "A Fundamental Approach to Transformer Thermal Modeling—Part II: Field Verification", IEEE Transactions of Power Delivery, vol. 16, No. 2, Apr. 2001, pp. 1-5.
Unknown, Author, "IEEE Guide for Loading Mineral-Oil-Immersed Transformers", IEEE Std C57.91-1995, Transformers Committee of the IEEE Power Engineering Society, Jun. 14, 1995, pp. 1-108.
Unknown, Author, "Intelligent Monitoring System, Type TEC—Technical Guide", ABB 1ZSC000857-ABG en, available online at: http://www05.abb.com/global/scot/scot252.nsf/veritydisplay/73c9c12318a02d82c12575370034321a/$file/1zsc000857-abg%20en.pdf, 2008, pp. 1-60.
Unknown, Author, "Power Transformers—Part 7: Loading Guide for Oil-Immersed Power Transformers", International Standard, IEC 60076-7, First Edition, Dec. 2005, pp. 1-64.
Unknown, Author, "TEC—Intelligent Transformer Monitoring System, Keeping an Eye on Your Transformer On-Line", ABB 1ZSC000857-ABN en, Rev. 3, available online at: http://www05.abb.com/global/scot/scot252.nsf/veritydisplay/84601cb411c55577c12577f1.00456dd7/$file/1zsc000857-abn%20en%20rev%203.pdf, publication date unknown, pp. 1-2.

* cited by examiner

METHOD AND APPARATUS FOR LEAKAGE MONITORING FOR OIL-IMMERSED ELECTRICAL TRANSFORMERS

STATEMENT REGARDING FEDERALLY SPONSORED RESEARCH OR DEVELOPMENT

This invention was made with U.S. Government support under Cooperative Agreement No. DE-OE0000547 awarded by the US Department of Energy (DOE). The Government has certain rights in this invention.

TECHNICAL FIELD

The present invention generally relates to oil-immersed power transformers such as used in the distribution of electricity, and particularly relates to leakage monitoring for such transformers.

BACKGROUND

Electrical transformers operate in the magnetic domain, using electromagnetic induction to transform voltage or current at one level into another level. Significant heat may be generated during transformer operation, as a consequence of copper losses, eddy losses and other stray losses. Transformer cooling thus represents a critical design element, particularly in the higher-power transformer applications seen in electrical generation, transmission and distribution.

Oil-based cooling, where the transformer windings and core are immersed in mineral oil, for example, represents a well-established technique for dissipating the heat generated during transformer operation. A number of references provide detailed thermal models of oil-immersed transformers, which may be used to predict operational temperatures for a given transformer, e.g., given winding current values and ambient temperature values. These mathematical representations of the thermal behavior of such transformers are seen, for example, in the following references: "Power Transformers—Loading Guide for Oil-Immersed Power Transformers," IEC 60076-7, first edition, 2005; "IEEE Guide for Loading Mineral-Oil-Immersed Transformer," IEEE Standard C57.91-1995, June 1995; D. Susa et al., "Dynamic thermal modelling of power transformers," IEEE Trans. Power Delivery, vol. 25, no. 1, pp. 197-204, January 2005.

Given the criticality of electrical power generation, transmission and distribution systems, and given the equipment expenses and safety and environmental issues implicated in the operation of oil-immersed transformers, there are a number of robust and highly sophisticated systems available for monitoring virtually every aspect of transformer health and operation. Consider, for example, the so-called "TEC" system offered by ABB. TEC is an electronic control, monitoring, and diagnostic device. The device is configured using a "fingerprint" of the transformer and it provides a single interface to the entire transformer with current and historical status data and the potential to predict loads. A minimum number of extra sensors is needed for TEC implementations, although with its modular nature, TEC provides support for richly instrumented and sophisticated transformer health monitoring and diagnostics.

Whether in the context of TEC-based monitoring, or transformer monitoring in a more general sense, it is known to monitor the operational status of transformer cooling systems, such as by monitoring the electrical current through the motors driving the involved cooling devices, which may be fans or pumps, or both. For example, a given oil-immersed transformer may be equipped with pumps to circulate its cooling oil through some type of heat exchanger. It is also known to monitor for oil leakage using a corresponding complement of sensors, such as pressure and temperature sensors, or using a low-density mobile mechanical device that floats within the transformer oil bath.

While these approaches offer valuable and detailed monitoring and diagnostic information, they can require significant amounts of transformer instrumentation, e.g., pressure sensors, current sensors, multiple temperature sensors, such as top oil and bottom oil temperature sensors, mechanical floats, etc. In certain installations, the costs and complexity of such instrumentation may be easily justified. Similarly, in the context of transformer manufacturing, it may not necessarily be a complicated or expensive proposition to build in a full complement of instrumentation sensors. However, it is recognized herein that there remains a range of applications where fully instrumenting transformers for diagnostic and health monitoring is not economic, such as where a system operator has hundreds or thousands of field-installed transformers that lack a full complement of instrumentation sensors.

SUMMARY

The present invention comprises an apparatus and method for detecting a loss of oil from an oil-immersed transformer, based on fitting a transformer top-oil temperature model to online measurements in an iterative optimization process that yields fitted values for a first model parameter representing the top-oil temperature rise over ambient temperature and a second model parameter representing the oil time constant. Among the several advantages seen in the contemplated apparatus and method is the reduction in required instrumentation, whereby transformer oil leaks are indirectly detected without requiring pressure sensors or mechanical floats, although the presence of such sensors is not excluded by the teachings herein.

Accordingly, an example method of monitoring for oil leakage from an oil-immersed electrical transformer includes determining characteristic values for the transformer, for first and second parameters of a top-oil temperature model, wherein the first parameter represents the top-oil temperature rise over ambient temperature and the second parameter represents the oil time constant. The method further includes obtaining online measurements for the transformer, including an ambient temperature measurement, a top-oil temperature measurement and a winding current measurement, and fitting the transformer top-oil temperature model to the online measurements in an iterative optimization process to obtain fitted values for the first and second parameters.

The example method further includes estimating a transformer oil thermal capacitance as a function of the fitted values and correspondingly estimating a transformer oil weight as a function of the estimated transformer oil thermal capacitance. Still further, the method includes generating alarm signaling based on comparing the estimated transformer oil weight to a characteristic transformer oil weight, as calculated from the characteristic values. By way of example, the comparing operation is performed on a filtered or time-qualified basis, such as where the alarm signaling is generated In a corresponding embodiment, an example apparatus is configured for monitoring for oil leakage from an oil-immersed electrical transformer. The apparatus includes at least one communication interface configured for at least one of: interfacing with one or more sensors that provide online measurements for the transformer, and interfacing with a supervisory computer system. The apparatus further includes a processing circuit that is operatively associated with the at least one communication interface.

The processing circuit, which may comprise microprocessor-based circuitry or other such digital processing circuitry, is configured to determine characteristic values for the transformer, for first and second parameters of a top-oil temperature model. As before, the first parameter represents the top-oil temperature rise over ambient temperature and the second parameter represents the oil time constant.

The processing circuit is further configured to obtain online measurements for the transformer, including an ambient temperature measurement, a top-oil temperature measurement and a winding current measurement. Correspondingly, the processing circuit is configured to fit the transformer top-oil temperature model to the online measurements in an iterative optimization process to obtain fitted values for the first and second parameters, and estimate a transformer oil thermal capacitance as a function of the fitted values and correspondingly estimating a transformer oil weight as a function of the estimated transformer oil thermal capacitance. The processing circuit is further configured to generate alarm signaling based on comparing the estimated transformer oil weight to a characteristic transformer oil weight, as calculated from the characteristic values.

Of course, the present invention is not limited to the above features and advantages. Those of ordinary skill in the art will recognize additional features and advantages upon reading the following detailed description, and upon viewing the accompanying drawings.

DETAILED DESCRIPTION

Figure 1:
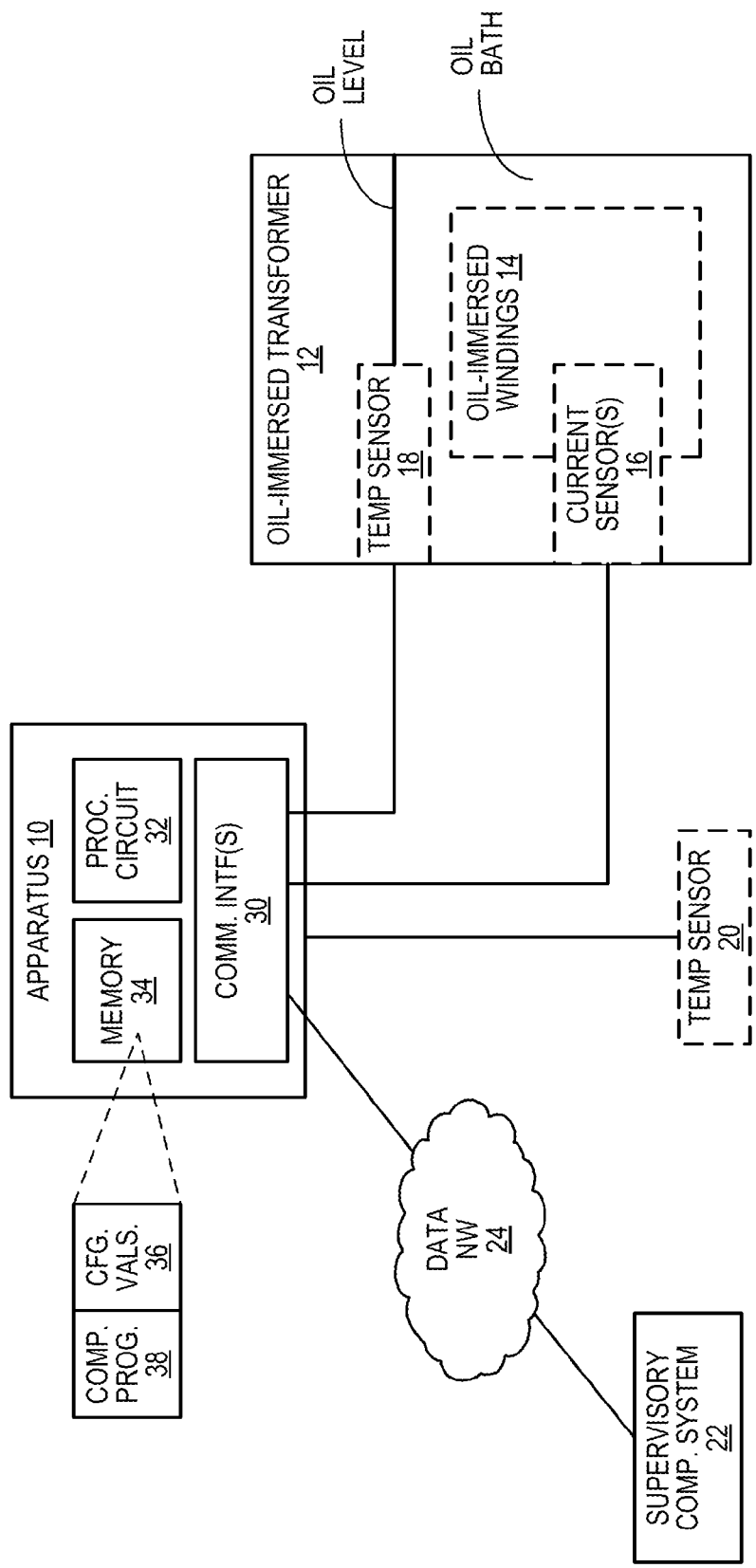
FIG. 1 is a block diagram of one embodiment of an apparatus as configured herein for monitoring for oil leakage from an oil-immersed power transformer.

FIG. 1 illustrates one example of an apparatus 10 as contemplated herein, where the apparatus 10 is configured for monitoring for oil leakage from an oil-immersed electrical transformer 12. The transformer windings 14, e.g., one or more primary windings and one or more secondary windings, are immersed in oil for cooling purposes and the transformer 12 includes at least minimum instrumentation comprising one or more current sensors 16, for sending winding current, and a temperature sensor 18, for sensing oil temperature at the top of the oil bath. That temperature is referred to as the top-oil temperature.

The apparatus 10 in the example arrangement is further associated with an ambient temperature sensor 20 and a supervisory computer system 22. For example, the supervisory computer system 22 is a type of Supervisory Control and Data Acquisition or SCADA system to which the apparatus 10 couples through a data network 24. As a non-limiting example, the supervisory computer system 22 is a grid automation controller, such as a "COM600" controller from ABB.

It will be understood that the apparatus 10 in some embodiments includes specific sensor inputs, e.g., to receive sensor signals from the current sensor(s) 16, the top-oil temperature sensor 18 and the ambient temperature sensor 20. However, it is specifically contemplated herein that the apparatus 10 in another embodiment will include one or more network interfaces such that it receives messages or other digital information conveying measurement data from any one or more of the involved sensors, meaning that the apparatus 10 does not necessarily have to have direct connections to such sensors, so long as it has timely access to the relevant measurement information.

Among its various circuitry, the apparatus 10 in the example arrangement of FIG. 1 includes one or more communication interfaces 30, a processing circuit 32 and associated memory 34, e.g., for storing configuration values 36 and a computer program 38. The communication interface(s) 30 include, for example, sensor interfaces for one or more of the current sensor(s) 16, the top-oil temperature sensor 18 and the ambient temperature sensor 20, along with a communication network interface for communicating with the supervisory computer system 22. The communication interface(s) 30 comprise analog signaling inputs, digital signaling inputs, or data communication inputs, or any mix thereof. As a non-limiting example, the communication interface(s) 30 includes a wireless radio transceiver, e.g., for local or wide area networking communications. Additionally, or alternatively, the communication interface(s) 30 include an Ethernet adaptor or other network interface card, along with associated protocol processors adapted for communicating with the supervisory communication system 22, e.g., over a packet data network such as the Internet.

The apparatus 10 thus includes at least one communication interface 30 configured for at least one of: interfacing with one or more sensors 16, 18 and 20 that provide online measurements for the transformer 12, and interfacing with a supervisory computer system 22. The processing circuit 32 is operatively associated with the at least one communication interface 30 and is configured to determine characteristic values for the transformer 12, for first and second parameters of a top-oil temperature model.

Here, the top-oil temperature model will be understood as a mathematical representation of the thermal behavior of the transformer 12 and is structured, for example, to output as its solution variable the top-oil temperature of the transformer 12 based on inputting measured winding current and measured ambient temperature. The top-oil temperature model is parameterized, for example, using a number of thermal parameters, including the aforementioned first and second parameters, wherein the first parameter represents the top-oil temperature rise over ambient temperature and the second parameter represents the oil time constant.

The processing circuit 32 is further configured to obtain online measurements for the transformer 12, including an ambient temperature measurement, a top-oil temperature measurement and a winding current measurement, e.g., real time or near real time measurements for the transformer 12 during live, online operation. Further, the processing circuit 32 is configured to fit the transformer top-oil temperature model to the online measurements in an iterative optimization process to obtain fitted values for the first and second parameters, and to estimate a transformer oil thermal capacitance as a function of the fitted values and correspondingly estimate a transformer oil weight as a function of the estimated transformer oil thermal capacitance. Correspondingly, the processing circuit 32 is configured to generate alarm signaling based on comparing the estimated transformer oil weight to a characteristic transformer oil weight, as calculated from the characteristic values.

The alarm signaling may be generated, for example, as one or more communication packets or messages, for transmission to the supervisory computer system 22 via the data network 24. Thus, in one or more embodiments, the processing circuit 32 is configured to output electronic signaling from the at least one communication interface 30 as the alarm signaling, for transmission to the supervisory computer system. Additionally, or alternatively, the alarm signaling may comprise local signal generation, such as for logging in a data record and/or for providing a human-detectable annunciation, such as audible or visible alarm signaling.

In some embodiments, the processing circuit 32 is configured to generate the alarm signaling based on comparing the estimated transformer oil weight to the characteristic transformer oil weight by determining whether or not the estimated transformer oil weight differs by more than a threshold amount from the characteristic transformer oil weight. That is, the comparison operation involves a comparison of the estimated transformer oil weight to the characteristic weight, which may be understood as a known-good reference weight, such as a factory-configured weight value or a weight value calculated during known-good operation conditions of the transformer 12.

Further, to avoid false alarms or excessive alarm signaling, in one or more embodiments the processing circuit 32 is configured to determine whether or not the estimated transformer oil weight differs by more than a threshold amount from the characteristic transformer oil weight for at least a defined number of evaluation cycles or for a duration in time that is longer than a defined evaluation window. The "comparison" operation is therefore filtered or otherwise time-qualified in a manner that causes the alarm signaling to be generated after the processing circuit 32 first ensures that the estimated transformer oil weight is out of bounds for some number of estimation intervals.

In the same or another embodiment, the processing circuit 32 is configured to determine the characteristic values based on being configured to perform at least one of: initialize the characteristic values to pre-configured factory values; and compute the characteristic values based on collected historical measurements for the ambient temperature, the top-oil temperature and the winding current. In other words, the characteristic values for any one or more of the transformer's top-oil temperature rise over ambient temperature, its oil time constant, and its oil weight may be pre-set or otherwise provisioned as part of the configuration values 36 loaded into the apparatus 10 at the time of its manufacture or at the time of its commissioning. In this regard, those of ordinary skill in the art will appreciate that the apparatus 10 can be paired with a specific transformer 12, or it can be associated with more than one transformer 12, with each transformer 12 being monitored separately in like manner by the apparatus 10, and with each transformer 12 potentially having its own set of characteristic values.

In at least one embodiment, the apparatus 10 is configured to characterize the transformer 12, i.e., to "learn" the characteristic values of the transformer 12, based on computing the characteristic values by fitting the transformer's top-oil temperature model to the historical measurements collected for the transformer 12 over a defined time window. The approach allows the apparatus 10 to obtain longer-term fitted values corresponding to the defined time window, which longer-term fitted values are stored as the characteristic values. In a non-limiting example, the apparatus 10 obtains online measurements for a given transformer over a defined time period—e.g., 24 hours, 36, hours, etc.—during which the transformer 12 is known to be "healthy," which means that it has a proper amount of cooling oil, its cooling system is in known-good working order, and it is otherwise operating normally.

During this window of observation, the processing circuit 32 obtains winding current measurements, ambient temperature measurements, and top-oil temperature measurements for the transformer 12 according to a defined evaluation cycle or period, e.g., every minute, every two minutes, or the like. At each evaluation interval, the processing circuit 32 performs a "reverse parameter estimation."

In "normal" model usage, the top-oil temperature model is populated with characteristic values for the top-oil temperature rise over ambient parameter and the oil time constant parameter, and those characteristic values are used to estimate the top-oil temperature as the model output, using measured values of winding current and ambient temperature as model inputs. Instead, with reverse parameter estimation, the values of the top-oil temperature rise over ambient temperature parameter and the oil time constant parameter are adjusted as needed to make the top-oil temperature value as output from the model agree with measured top-oil temperature, in view of the measured ambient temperature and winding current values.

Thus, by performing such reverse estimation during a period of known-good operation, and especially by repeating the reverse parameter estimation a number of times over some time window of known-good operation and, e.g., averaging the reverse-estimated characteristic values, the apparatus 10 learns the characteristic values for the transformer 12 and can store those characteristic values for later use in determining whether the transformer 12 is experiencing an abnormal operating condition, e.g., such as a low oil level. In at least one embodiment, the processing circuit 32 is configured to repeat the fit, estimate and generate operations according to a defined leak-checking time interval.

That is, assuming that it has provisioned or learned characteristic values for the relevant model parameters in its top-oil temperature model, the processing circuit 32 obtains online measurements for the ambient temperature, winding current, and top-oil temperature for the transformer 12, and uses those values to reverse-estimate the key model parameter values, which it then checks for agreement with the characteristic values of those parameters. Such checking can be done, e.g., every minute, every five minutes, or at some other programmed evaluation interval.

As for performing the fitting during a given evaluation cycle or operation, the processing circuit 32 in one or more embodiments is configured to carry out an iterative optimization process, wherein it iteratively adjusts the values of the first and second parameters (i.e., the top-oil temperature rise over ambient temperature parameter and the oil time constant parameter) in the top-oil temperature model, to minimize the error between the top-oil temperature measurements and top-oil temperature estimates, as estimated from the top-oil temperature model. For example, in at least one embodiment, the processing circuit 32 is configured to iteratively adjust the values of the first and second parameters by closing an error feedback loop through an optimization algorithm that adjusts the values of the first and second parameters.

These adjustments are based on the processing circuit 32 feeding back the error between the top-oil temperature measurements and top-oil temperature estimates as an input to the optimization algorithm. The optimization algorithm is a Nelder-Mead optimization algorithm in one example. Of course other optimization algorithms may be used, for example, there are any number of heuristic optimization algorithms that can be used to adjust or fit the model parameters as needed, so that the error is minimized between the measured top-oil temperature and the top-oil temperature estimate output from the model. In performing such fitting, it will be appreciated that the processing circuit 32 is configured to obtain the online measurements for the transformer 12 by receiving, via the at least one communication interface 30, electronic signaling directly or indirectly from sensors sensing the ambient temperature in a vicinity of the transformer 12, the top-oil temperature of the oil in the transformer 12, and the winding current in at least one of a primary and a secondary winding of the transformer 12.

Figure 2:
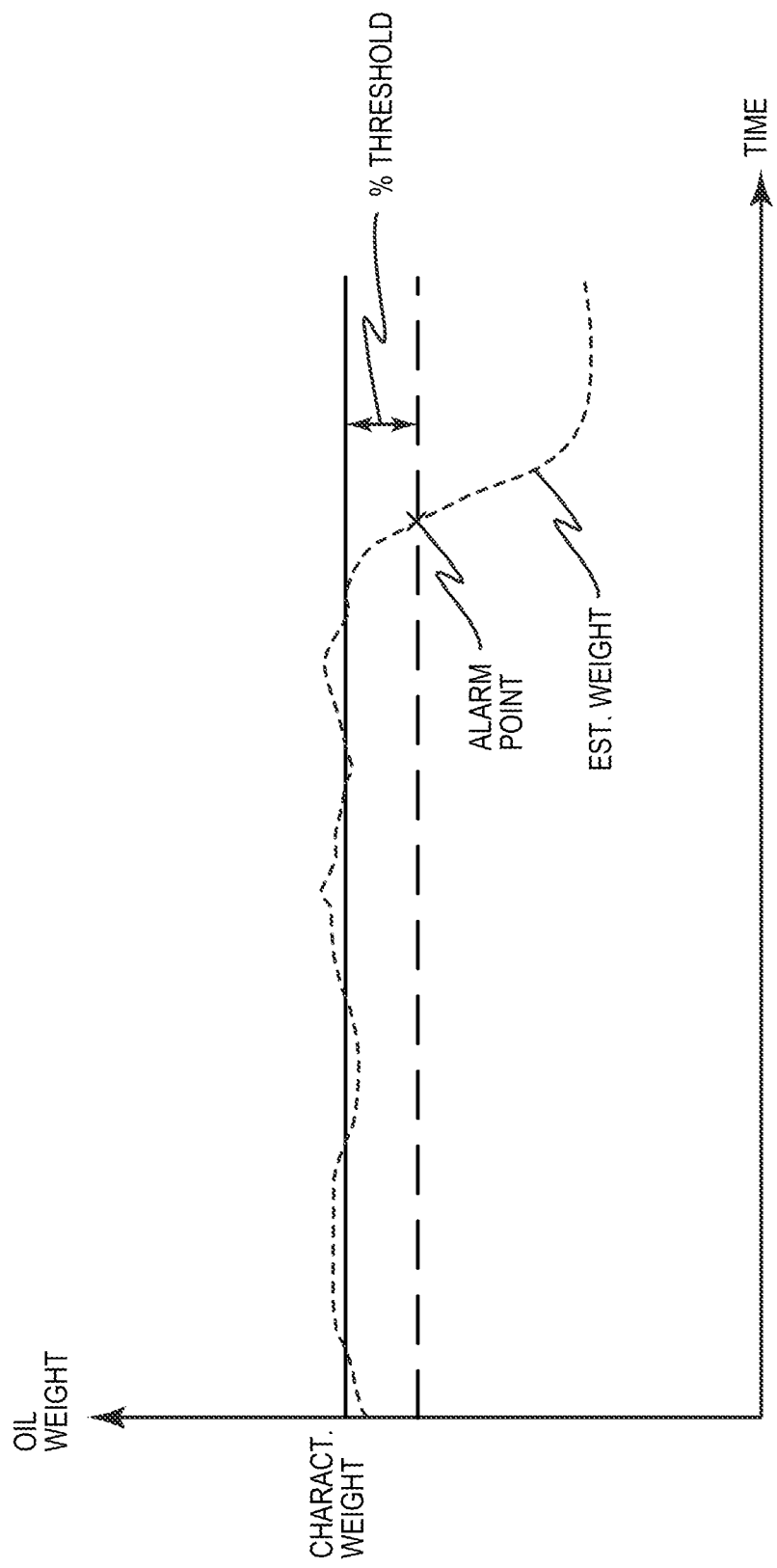
FIG. 2 is a plot of example characteristic and estimated transformer oil weights, and a corresponding alarm threshold.

FIG. 2 provides an example plot of how the estimated transformer oil weight, as obtained from the above-described reverse-parameter estimation processing, tracks the characteristic transformer oil weight on a relatively close basis during normal operation, but deviates significantly if meaningful amounts of the oil are lost due to leakage. The processing circuit 32 therefore is, for example, configured to compare the estimated transformer oil weight to the characteristic weight and to generate alarm signaling if the estimated transformer oil weight falls below the characteristic transformer oil weight by more than a defined threshold. The alarm threshold may be defined on a relative basis, e.g., ninety percent or ninety-five percent of the characteristic value of the transformer oil weight.

Figure 3:
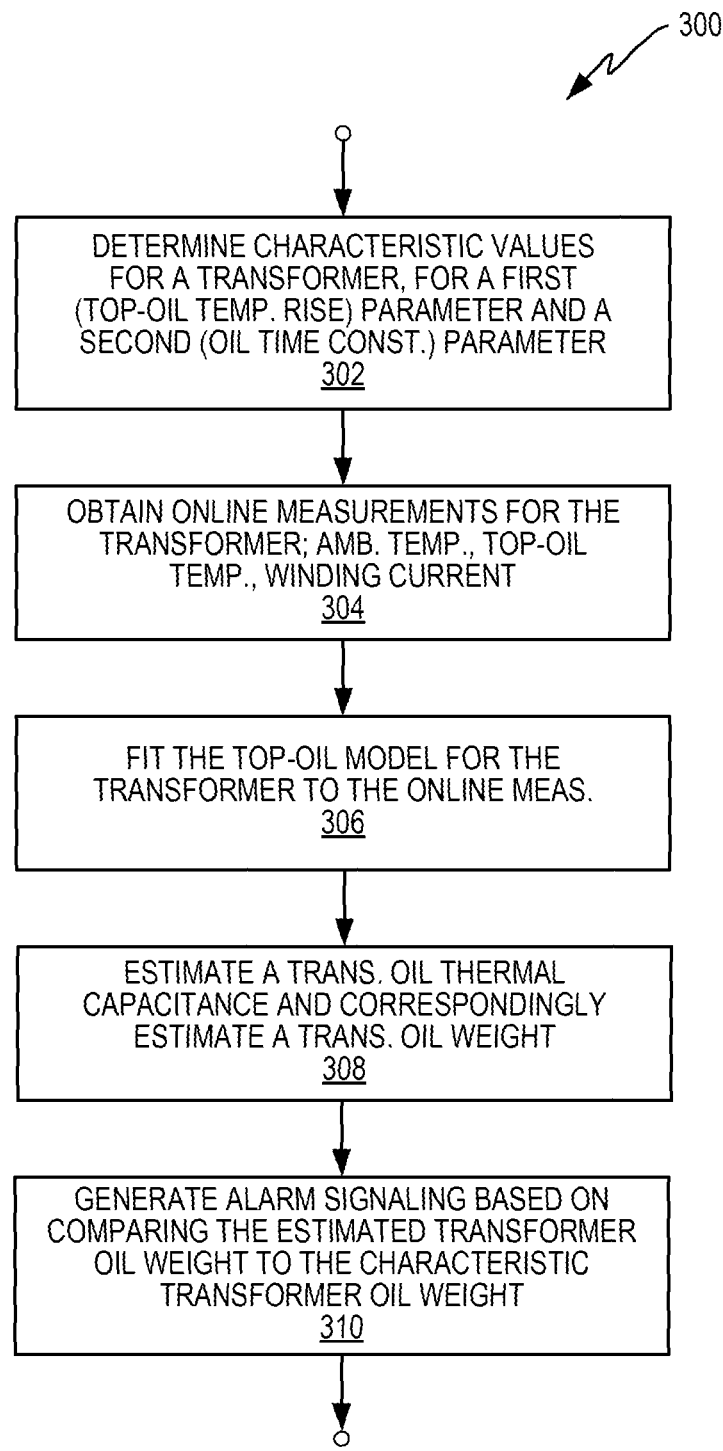
FIG. 3 is a logic flow diagram of one embodiment of a method of detecting oil leakage from an oil-immersed power transformer, such as may be implemented in the apparatus of FIG. 1.

FIG. 3 illustrates one embodiment of a method 300, such as is implemented by the apparatus 10 through appropriate configuration of the processing circuit 32. In one example the processing circuit 32 comprises a microprocessor, a microcontroller, a Digital Signal Processor (DSP), a Field Programmable Gate Array (FPGA), a Complex Programmable Logic Device (CPLD), or an Application Specific Integrated Circuit (ASIC), or any mix thereof. Further, the processing circuit 32 may, in actual implementation, comprise more than one processing circuit operating in cooperative fashion. However implemented, the digital processing circuitry comprising the processing circuit 32 is, in one or more embodiments, specially adapted to carry out the processing and control algorithms disclosed herein based on its execution of computer program instructions comprising the computer program 38.

The memory 34, which may comprise one memory or storage device, or multiple devices, can be broadly understood as one or more types of computer readable media that provide non-transitory storage for the computer program 38. As a non-limiting example, the memory 34 comprises volatile memory or non-volatile memory, or a mix of both. For example, the memory 34 includes one or more SRAM or DRAM memory circuits, along with FLASH, EEPROM, or other non-volatile memory circuits. In similar fashion, the memory 34 provides for non-transitory storage of the configuration values 36, which comprise or include the aforementioned characteristic values associated with the top-oil temperature model used by the processing circuit 32. Of course, the "non-transitory" designation here does not mean that such values cannot be updated or replaced with new values.

With the above points in mind, the method 300 "begins" with the processing circuit 32 determining characteristic values for the transformer 12 (Block 302), for first and second parameters of a top-oil temperature model. The first parameter represents the top-oil temperature rise over ambient temperature and the second parameter represents the oil time constant. As previously explained, the model takes as its inputs winding current measurements and ambient temperature measurements, and produces as its output an estimate of the top-oil temperature. That output depends on the values used in the model for the top-oil temperature rise over ambient temperature parameter and for the oil time constant parameter.

Thus, by reverse-estimating the parameter values based on fitting the model output to observed top-oil temperature values during normal operation of the transformer 12, the processing circuit 32 thereby obtains the characteristic values for the parameters—i.e., values that are associated with normal operation of the transformer 12. This determination of characteristic values can be done once, e.g., whenever the transformer 12 is initially put into service, or can be done (or repeated) at any point in time—although determination of the characteristic values preferably will be only if or when the transformer 12 is known to be in good working order, so that they reflect "normal" values.

Further, as previously noted, the transformer 12 may have already been characterized or its characteristic values may otherwise be known, and such values may be loaded into the apparatus 10 and used as is, without need for the foregoing "learning" process. Still further, the apparatus 10 may start off with provisioned characteristic values and then later update or replace those provisioned values based on learning them from observed online measurements. Such updating may be performed by the apparatus 10 by placing it into a calibration mode, which in one or more embodiments is accomplished by input control signaling via the one or more communication interface(s) 30. The apparatus 10 can therefore calibrate its operation to essentially any particular transformer 12 based on processing online measurements for that transformer 12, and can re-calibrate as needed or commanded, e.g., to account for transformer aging, or other changes affecting the thermal performance of the transformer 12.

Regardless of whether the characteristic values are provisioned or learned, the method 300 further includes obtaining online measurements for the transformer 12 (Block 304), including an ambient temperature measurement, a top-oil temperature measurement and a winding current measurement. Here, it will be understood that these online measurements correspond to a time or times during which the operational health of the transformer is not necessarily known. Thus, the measurements are obtained so as to determine whether an oil leak has occurred and the method 300 includes fitting the transformer top-oil temperature model to the online measurements in an iterative optimization process to obtain fitted values for the first and second parameters (Block 306).

The method 300 further includes estimating a transformer oil thermal capacitance as a function of the fitted values and correspondingly estimating a transformer oil weight as a function of the estimated transformer oil thermal capacitance (Block 308). Still further, the method 300 includes generating alarm signaling based on comparing the estimated transformer oil weight to a characteristic transformer oil weight (Block 310), as calculated from the characteristic values (i.e., the characteristic values of the key thermal model parameters).

Figure 4:
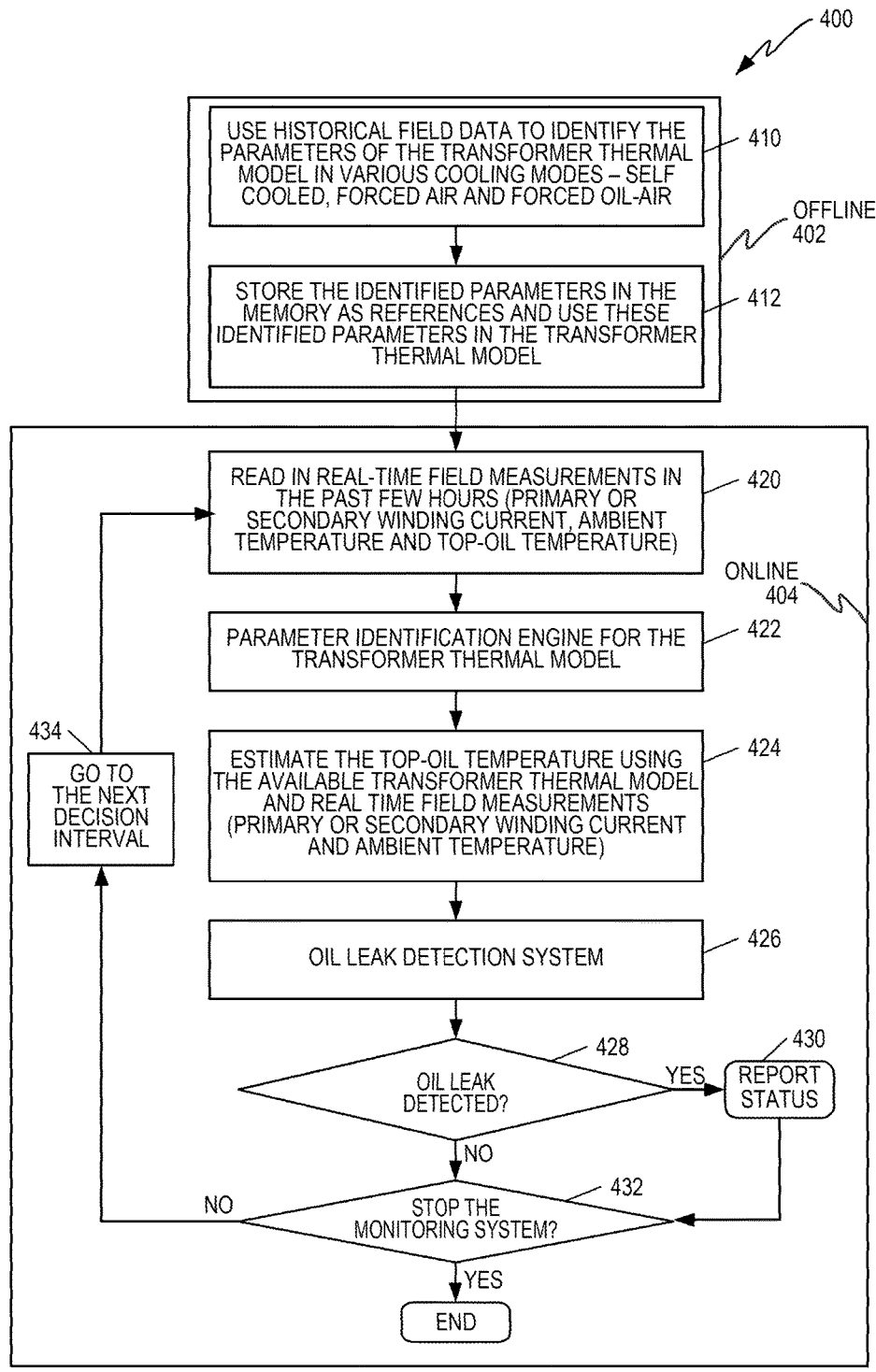
FIG. 4 is a logic flow diagram another embodiment of a method of detecting oil leakage from an oil-immersed power transformer, such as may be implemented in the apparatus of FIG. 1.

FIG. 4 illustrates an example embodiment of the method 300, where this more detailed, example implementation is labeled as a method 400. One sees that the method 400 includes an offline portion 402 and an online portion 404. The offline portion is referred to as being "offline" not to denote that the transformer 12 itself is offline, but to denote that the processing at issue is directed to determining the characteristic values that will be subsequently used for online monitoring of transformer health by the apparatus 10 rather than to monitoring transformer health.

The offline portion 402 includes processing operations labeled as Blocks 410 and 412, and these operations include using historical field data for the transformer 12—e.g., a set of actual measurements for the transformer 12 for ambient temperature and corresponding measurements for top-oil temperature and winding current, for the transformer 12. The data may be collected over a defined window of time, or over different times, and can be collected for any number of operational modes of the transformer's cooling system, to the extent that the cooling system has different operational modes. The collected data is used to reverse-estimate characteristic values for the top-oil temperature model of the transformer, including estimating a characteristic value for the top-oil temperature rise over ambient temperature, and a characteristic value for the oil time constant. As explained before, these parameters are used in the top-oil temperature model, to estimate the top-oil temperature for the transformer 12—i.e., the oil temperature at the top of the oil bath—for a given set of input measurements, including measured ambient temperature, and measured winding current.

The online portion 404 includes a number of processing operations labeled as Blocks 420-434 (even). The processing operations can be understood as illustrating the repeated, looping nature of the online monitoring, whereby the apparatus 10 repeatedly, e.g., periodically, checks for oil leakage. At a given evaluation or decision interval, such processing includes reading in measurements in real time, which here means that the measurements were obtained for, e.g., the most recent last few hours of operation (Block 420). The measurements are used to reverse-estimate the top-oil temperature rise over ambient temperature parameter and the oil time constant parameters in the top-oil temperature model of the transformer 12 (Blocks 422 and 424). That is, the apparatus 10 uses the read-in measurements for winding current and ambient temperature as inputs to the top-oil temperature model, to produce top-oil temperature estimates, and it adjusts the model parameters to minimize the error between those estimates and the corresponding actual measurements of top-oil temperature, as read in as part of the same online data set.

The reverse-estimated model parameter(s) are then compared to the corresponding characteristic value(s), and alarm signaling is generated in dependence on the results of such comparison (Blocks 426 and 428). Further processing includes reporting the determined transformer status (Block 430), and determining whether to continue monitoring (Block 432), which is the default or normal choice, and if so to continue onto the next evaluation or decision interval (Block 434). This looping can be understood as repeating the online processing portion 404, with a new data set that includes the most recent online measurements for the transformer 12.

Figure 5:
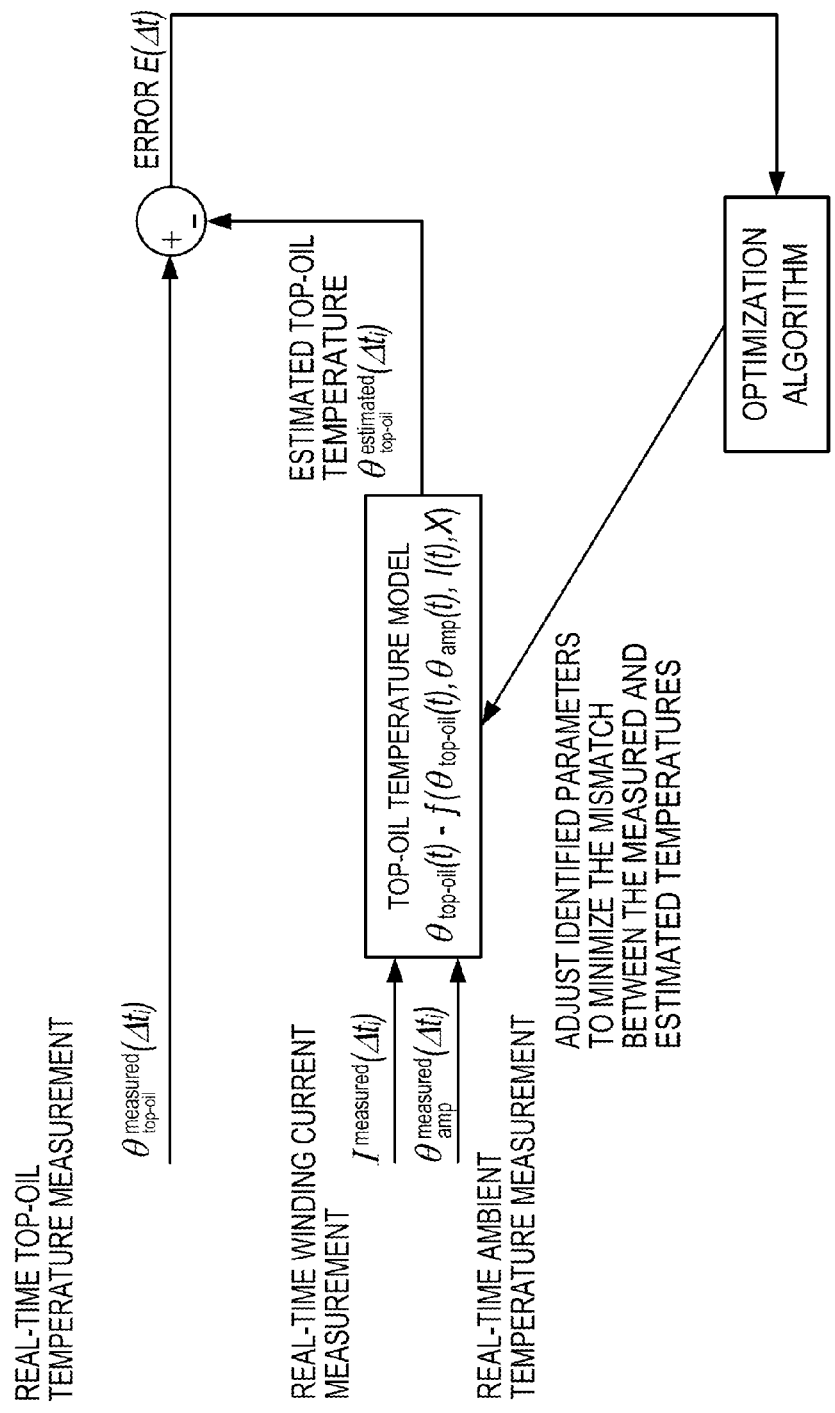
FIG. 5 is a logic flow diagram illustrating one embodiment of an iterative fitting process as used to fit a top-oil temperature model for a transformer to online measurements.

FIG. 5 illustrates an example implementation of the contemplated reverse-estimation process, which is also referred to as a "fitting" process in which the model parameters are fitted so as to minimize the error between the model-estimated top-oil temperature and the actual measurements of top-oil temperature. One sees actual winding current measurements and ambient temperature measurements as being the model inputs to a top-oil temperature model. Further one sees the model producing top-oil temperature estimates as the model output, which estimates are then compared to the corresponding top-oil temperature measurements, e.g., as obtained from the temperature sensor 18 seen in FIG. 1. The error from that comparison is then fed back to an optimization algorithm that adjusts the identified model parameters—the top-oil temperature rise over ambient temperature parameter and the oil time constant parameter—so as to minimize the error.

In more detail, the inputs include the ambient temperature $T_{amb}(\Delta t)$, the transformer top oil temperature $T_{top-oil}(\Delta t)$, and the transformer winding current (either primary or secondary side) measurements, denoted as $I(\Delta t)$. The outputs include: the estimated parameters of the top-oil temperature model and the estimated winding hot-spot and top-oil temperatures, and a normal/abnormal status and associated alarm signaling, as needed, regarding the transformer oil level status. As noted, the configuration values 36 may include the relevant thermal model parameters or placeholders and user settings.

When an oil leak occurs, the thermal capacitance of the transformer oil will be decreased due to the lost volume. The real-time detection of oil leakage helps operators timely detect extent or impending transformer failures, extend the life of the transformer 12, and avoid costly unplanned outages. The rated oil time constant and the rated top-oil temperature rise over the ambient temperature in the transformer thermal model are estimated in each decision interval of a few minutes using the real-time data of the past few hours. The decision interval and the duration of the real-time data may be specified by users or set to default values, such as five minutes for the decision interval and four hours for historical data window.

The dynamic thermal model of an oil-immersed transformer provides estimates of the winding hot-spot temperature and the top-oil temperature using the ambient temperature and the winding current, either primary or secondary, as inputs. For example, existing literature proposes at least three dynamical thermal models for oil-immersed transformers, as explained in the Background of this document. Consider, for example, the following expressions and definitions:

$$k_{11}\tau_{oil,rated}\frac{d\theta_{top-oil}}{dt} = \left(\frac{1+R\cdot K^2}{1+R}\right)^x \cdot \Delta\theta_{top-oil,rated} - \left(\theta_{top-oil} - \theta_{amb}\right)$$

$$\Delta\theta_{hot-spot} = \Delta\theta_{hot-spot1} - \Delta\theta_{hot-spot2}$$

$$k_{22}\tau_{wnd,rated}\frac{d\Delta\theta_{hot-spot1}}{dt} = k_{21}\cdot K^y \cdot \Delta\theta_{hot-spot,rated} - \Delta\theta_{hot-spot1}$$

$$\tau_{oil,rated}/k_{22}\frac{d\Delta\theta_{hot-spot2}}{dt} = (k_{21}-1)\cdot K^y \cdot \Delta\theta_{hot-spot,rated} - \Delta\theta_{hot-spot2}$$

$$\theta_{hot-spot} = \theta_{top-oil} + \Delta\theta_{hot-spot}$$

$$K = I(t)/I_{rated}$$

where, t is the time variable, $k_{11}$, $k_{21}$, and $k_{22}$ are coefficients of the thermal model; and $\tau_{oil,\,rated}$ $\tau_{wind,\,rated}$ are the oil and winding time constant parameters; $\theta_{amb}$, $\theta_{top-oil}$ and $\theta_{hot-spot}$ are ambient, top-oil and hot-spot temperatures, respectively; x and y are the oil and winding exponents; $\Delta\theta_{top-oil,\,rated}$ is the top-oil temperature rise over ambient temperature parameter; K is the load factor; I(t) is the winding current; $I_{rated}$ is the rated current of the transformer; and R is the ratio of load losses at rated current to no-load losses.

Thus, with respect to prior descriptions of reverse parameter estimation, the model parameters subject to reverse-estimation include or comprise the oil time constant parameter $\tau_{oil,\,rated}$ and the top-oil temperature rise over ambient temperature parameter $\Delta\theta_{top-oil,\,rated}$. The reader should note that the use of the word "rated" in the variables used to represent these parameters stems from the fact that a given transformer 12 generally will have rated or designed-for values for these parameters. However, these values may not be known for a given transformer and may change over time and can be provisioned or learned according to the teachings herein. Further, these variables are recalculated during the reverse parameter estimation taught herein, in order to minimize the error between estimated and observed top-oil temperatures, and the deviation of those recalculated values from the corresponding characteristic values serves as an indication of abnormal transformer conditions, e.g., low oil levels.

According to a conventional IEEE thermal model:

$$\tau_{oil,rated} \frac{d\theta_{top-oil}}{dt} = \left(\frac{1+R\cdot K^2}{1+R}\right)^n \cdot \Delta\theta_{top-oil,rated} - (\theta_{top-oil} - \theta_{amb})$$

$$\tau_{wnd,rated} \frac{d\Delta\theta_{hot-spot}}{dt} = \left(\frac{1+R\cdot K^2}{1+R}\right)^m \cdot \Delta\theta_{hot-spot,rated} - (\theta_{hot-spot} - \theta_{top-oil})$$

where, n and m are the oil and winding exponents; and $\Delta\theta_{hot-spot,\,rated}$ is the rated hot-spot temperature rise over top-oil temperature.

In an improved model, the following relationships are defined:

$$\tau_{oil,rated} \frac{d\theta_{top-oil}}{dt} = \frac{1+R\cdot K^2}{1+R} \cdot \Delta\theta_{top-oil,rated} - \frac{(\theta_{top-oil} - \theta_{amb})^{n_1+1}}{\mu_{pu}^{n_1} \cdot \Delta\theta_{top-oil,rated}^{n_1}}$$

$$\tau_{wnd,rated} \frac{d\Delta\theta_{hot-spot}}{dt} = [K^2 \cdot P_{cu,pu}(\theta_{hot-spot})] \cdot \Delta\theta_{hot-spot,rated} - \frac{(\theta_{hot-spot} - \theta_{top-oil})^{n_2+1}}{\mu_{pu}^{n_2} \cdot \Delta\theta_{hot-spot,rated}^{n_2}}$$

$$\mu = \mu_{rated}\mu_{pu} \quad \mu = 0.0000013573 \cdot \exp\left[\frac{2797.3}{\theta_{top-oil} + 273}\right]$$

$$\mu_{rated} = 0.0000013573 \cdot \exp\left[\frac{2797.3}{\theta_{top-oil,rated} + 273}\right]$$

$$P_{cu,pu}(\theta_{hot-spot}) = \frac{P_W}{P_W + P_E} \cdot \frac{\theta_r + \theta_{hot-spot}}{\theta_r + \theta_{hot-spot,rated}} + \frac{P_E}{P_W + P_E} \cdot \frac{\theta_r + \theta_{hot-spot,rated}}{\theta_r + \theta_{hot-spot}}$$

where $n_1$ and $n_2$ are the oil and winding exponents, $P_W$ and $P_E$ are DC and eddy losses, $\theta_{hot-spot\,rated}$ is the rated hot-spot temperature; and $\theta_r$ may be chosen as 234 for copper or 228 for aluminum.

The accuracy of the improved model is higher than the IEEE and IEC models (actual temperature measurements for power transformers –250-605 MVA are used in the comparison). All three models referenced in the Background may be integrated into the apparatus 10 and the apparatus 10 can be configured so that a user specifies which of the stored thermal models to use. Further, the apparatus 10 in one or more embodiments is configured to allow the user to load a user-defined thermal model, and to use the loaded user-defined thermal model for oil leak detection as taught herein.

Regardless of the model specifics, a general expression of the applicable dynamic thermal model can be given for the top-oil temperature as:

$$\dot{\theta}_{top-oil}(t) = f(\theta_{top-oil}(t), \theta_{amb}(t), I(t), X) \quad \text{Top-oil temperature model:}$$

$$\dot{\theta}_{hot-spot}(t) = g(\theta_{hot-spot}(t), \theta_{top-oil}(t), I(t), X) \text{ Hot-spot temperature model:}$$

where, X is the parameter vector of the transformer thermal model, which includes the aforementioned time constant parameters for the oil and the transformer windings and winding exponents, the rated top-oil and hot-spot temperature rise over ambient temperature parameters, along with the rated top-oil and hot-spot temperatures, and other applicable coefficients.

With reference again to FIG. 4, the offline portion 402 of the method 400 includes determination of the characteristic values for the transformer thermal model parameters, including the rated oil time constant $\tau_{oil,\,rated}$ and the rated top-oil temperature rise over the ambient temperature $\Delta\theta_{top-oil,\,rated}$. The characterization process uses normal historical field data including primary or secondary winding current, ambient temperature and top-oil temperature. These two parameters may also be provided pre-configured rather than learned, e.g., provided by the transformer manufacturer. The parameters of the transformer thermal model in three different cooling modes, e.g., self-cooled mode, forced-air cooling mode, and forced oil-air cooling mode, if applicable, are estimated separately. The estimated parameters are stored in the memory as the characteristic values of those parameters—the characteristic values may thus be regarded as the reference values that are used for monitoring transformer health.

During the online portion 404 of the method 400, the transformer oil leak detection algorithm is executed in near real-time. For each decision point, the procedure may be executed to indirectly (inferentially) check the oil level. The decision interval may be specified by the user or set to a default value of, for example, one minute. The real-time field measurements including the primary or secondary winding current, the top-oil temperature, and the ambient temperature as obtained over the defined measurement interval are read into the memory 34 by the processing circuit 32, for use in reverse-estimating the oil time constant and top-oil temperature rise over ambient parameters of the transformer thermal model. The reverse-estimated values of these parameters are compared to the corresponding characteristic values, as a mechanism to detect oil loss.

As explained, the processing circuit 32 reverse-estimates the oil time constant parameter and the top-oil temperature rise over ambient temperature parameter using an optimization solver driven from actual online measurements obtained for the transformer 12. The optimization solver searches the optimal thermal model parameters to minimize the mismatch between the model output of estimated top-oil temperature and the actual measurements of top-oil temperature. The hot-spot temperature model is not included in the system identification problem. Thus, the reverse-estimated parameter vector is defined as $\hat{X}=[\tau_{oil,\,rated}\,\Delta\theta_{top-oil,\,rated}]$. The top-oil temperature model used in the parameter estimation engine is expressed as $\theta_{top-oil}(t)=f(\theta_{top-oil}(t),\,\theta_{amb}(t),\,I(t),\,\hat{X})$. The model inputs include the measured primary or secondary winding RMS current $I^{measured}(t)$ and the measured ambient temperature $\theta_{amb}^{measured}(t)$, with the output being the estimated top-oil temperature $\theta_{top-oil}^{estimated}(t)$.

With reference to FIG. 5, the least square error of the estimated and measured top-oil temperature data is defined as the objective function in the optimization problem. The optimization algorithm comprises, for example a heuristic optimization algorithm. In at least one embodiment, the processing circuit 32 implements the Nelder-Mead method as an optimization solver to search the optimal values of the top-oil temperature model parameters. This method is a local optimization method and can search the optimal solution in hundreds of iterations, while still finishing its computations in a reasonable time.

To detect abnormal status of the transformer, the parameter estimation procedure may be executed periodically e.g. every one minute. For each evaluation cycle or interval, the parameter estimation procedure is executed by the processing circuit 32 to update the estimated parameters using the updated field data. The newly reverse-estimated values for the parameters $[\tau_{oil,\,rated}^{identified}\,\Delta\theta_{top-oil,\,rated}^{identified}]$ are compared with the characteristic values preconfigured or learned for those parameters, $[\tau_{oil,\,rated}^{ref}\,\Delta\theta_{top-oil,\,rated}^{ref}]$, to detect abnormalities.

Figure 6:
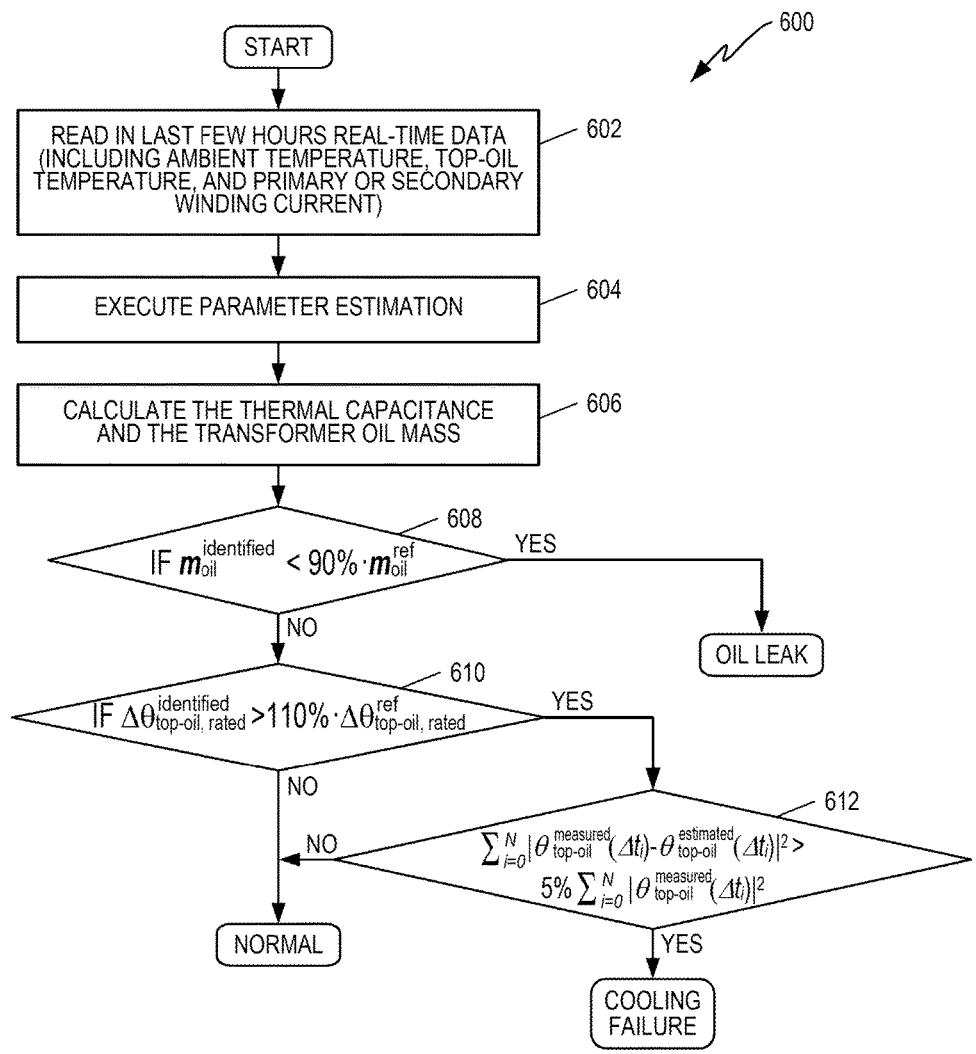
FIG. 6 is a logic flow diagram illustrating example details for implementing the method of FIG. 3 or 4.

FIG. 6 illustrates yet another detailed example of the method 400 introduced in FIG. 4. The processing set forth in FIG. 6 is labeled as a method 600. For each evaluation interval, the most current set of field data, including the ambient temperature, the top-oil temperature, and the primary or secondary winding RMS current, are read into the memory 34 by the processing circuit 32 (Block 602). Using this field data, the parameter estimation engine as implemented by the processing circuit 32 estimates the rated top-oil temperature rise over the ambient temperature, $\Delta\theta_{top-oil,\,rated}^{identified}$, and the rated oil time constant (Block 604).

The transformer oil thermal capacitance is calculated (Block 606), for example, using the following equation:

$$C_{th-oil}^{identified} = \frac{\tau_{oil,rated}^{identified} \cdot q_{losses,rated}}{3600 \cdot \Delta\theta_{oil,rated}^{identified}}$$

where, $\tau_{oil,\,rated}^{identified}$ is the estimated rated oil time constant (sec); $\Delta\theta_{oil,\,rated}^{identified}$ is the estimated rated top-oil temperature rise (° C.); $q_{losses,\,rated}$ is the total supplied loss (W) at the rated load; and $C_{th-oil}^{identified}$ is the estimated equivalent thermal capacitance of the transformer oil (Wh/° C.).

The oil thermal capacitance linearly depends on the weight of the transformer oil, which is expressed as follows.

$$m_{oil}^{identified} = C_{th-oil}^{identified}/0.48$$

where, $m_{oil}^{identified}$ is the estimated weight of the transformer oil in kg. Thus, the processing of Block 606 will also be understood as including the estimation of the transformer oil weight from the calculated thermal capacitance.

The reference or characteristic value for transformer oil weight is expressed as follows.

$$m_{oil}^{ref} = \frac{\tau_{oil,rated}^{ref} \cdot q_{losses,rated}}{3600 \cdot \Delta\theta_{oil,rated}^{ref} \cdot 0.48}$$

where, $\tau_{oil,\,rated}^{ref}$ and $\Delta\theta_{oil,\,rated}^{ref}$ are the estimated parameters using the transformer normal operation data in the offline portion 402 of the method 400 as shown in FIG. 4.

If the estimated transformer oil weight is less than for example ninety percent of the characteristic transformer oil weight, i.e., the reference value $m_{oil}^{ref}$, the oil leak alarm is asserted (YES from Block 608). Alarm assertion may be subjected to filtering or other time qualification. One advantage of using a multiplier for the alarm threshold is that it accounts for intrinsic errors in the estimation process and field measurements. This threshold may be adjusted upwards or downwards based on the sensitivity requirements from the user's perspective, where "user" here denotes personnel of the transformer owner or operator that are responsible for configuring or installing the apparatus 10.

FIG. 6 also illustrates additional parameter checking that may be advantageous as a supplement to the oil leak check. In particular, if the estimated top-oil temperature rise $\Delta\theta_{top-oil,\,rated}^{identified}$ is less than one-hundred-and-ten percent of the reference value $\Delta\theta_{top-oil,\,rated}^{ref}$ (NO from Block 610), then the transformer cooling system is deemed healthy by the processing circuit 32. Otherwise (YES from Block 610), the processing circuit 32 performs an additional check. Namely, in Block 612 it determines whether or not $$\Sigma_{i=1}^{N}|\theta_{top-oil}^{measured}(\Delta t_i)-\theta_{top-oil}^{estimated}(\Delta t_i)|^2 < 5\% \cdot \Sigma_{i=1}^{N}|\theta_{top-oil}^{measured}(\Delta t_i)|^2$$

where, N is the number of the data points used in the estimation. If the sum squared error of the estimated and measured top-oil temperatures is less than a threshold e.g. five percent of the sum squared measured top-oil temperature, the cooling system is considered healthy; otherwise, the cooling failure is asserted. The thresholds e.g. 110% and 5% are used to reduce the risk of misdetection due to intrinsic errors in the parameter estimation and in the field measurements.

Thus, according to the teachings herein, a method and apparatus for oil leakage detection is provided, where such detection is advantageously based on monitoring the transformer oil thermal capacitance in real time or near real time. The oil thermal capacitance linearly depends on the total oil weight in the tank. When oil leaks, the decrease in the oil weight leads to decreased oil thermal capacitance. While such instrumentation is not excluded from use, there is no need for an oil pressure sensor or low density floating mobile mechanical devices to perform oil leak detection using the contemplated apparatus and method. Obviating the need for such instrumentation reduces costs and complexities, which in turn makes the teachings herein readily applicable to a wide range of new and existing transformer installations, including cost-constrained medium voltage applications.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

What is claimed is:

1. A method of monitoring for oil leakage from an oil-immersed electrical transformer comprising:
measuring, using at least a top-oil temperature sensor, a top-oil temperature of an oil of the oil-immersed electrical transformer;
measuring, using at least a temperature sensor, an ambient temperature;
measuring, using at least a current sensor, a winding current of at least one winding of the oil-immersed electrical transformer;
communicating, using a communication interface that is configured for interfacing with the top-oil temperature sensor, the temperature sensor, and the current sensor, online measurements comprising the ambient temperature measurement, the top-oil temperature measurement, and the winding current measurement;
determining, by a processing circuit, characteristic values for first and second parameters of a transformer top-oil temperature model, wherein the first parameter represents a top-oil temperature rise over ambient temperature and the second parameter represents an oil time constant, and wherein the characteristic values for the first and second parameters comprises at least one of pre-configured factory values and collected historical measurements;
estimating, by the processing circuit and using at least the determined characteristic values for the first and second parameters with the transformer top-oil temperature model, a top-oil temperature;
comparing, by the processing circuit, the estimated top-oil temperature to the on-line measurements;
fitting, by the processing circuit and in response to the comparison of the estimated top-oil temperature to the on-line measurements and in an iterative optimization process, the first and second parameters to obtain fitted characteristic values for the first and second parameters;
estimating, by the processing circuit, a transformer oil thermal capacitance as a function of the fitted characteristic values and correspondingly estimating a transformer oil weight as a function of the estimated transformer oil thermal capacitance;
generating, by the processing circuit, alarm signaling, based on comparing the estimated transformer oil weight to a characteristic transformer oil weight, the characteristic transformer oil weight being calculated from at least the characteristic values for the first and second parameters and
generating, by the processing circuit, a maintenance diagnostic of the oil-immersed electrical transformer based on the generated alarm signaling, the maintenance diagnostic implemented by the oil-immersed electrical transformer to detect a loss of oil from the oil-immersed electrical transformer.

2. The method of claim 1, wherein determining the characteristic values comprises at least one of:
initializing the characteristic values to the pre-configured factory values; and
computing the characteristic values based on the collected historical measurements for the ambient temperature, the top-oil temperature and the winding current.

3. The method of claim 2, wherein computing the characteristic values based on the collected historical measurements comprises fitting the transformer top-oil temperature model to the historical measurements collected over a defined time window, to thereby obtain historical fitted characteristic values corresponding to the defined time window, which historical fitted characteristic values are stored as the characteristic values.

4. The method of claim 1, wherein the steps of fitting, estimating transformer oil thermal capacitance as a function of the fitted characteristic values and correspondingly estimating a transformer oil weight as a function of the estimated transformer oil thermal capacitance, and generating are repeated according to a defined leak-checking time interval.

5. The method of claim 1, wherein generating the alarm signaling based on comparing the estimated transformer oil weight to the characteristic transformer oil weight comprises determining whether or not the estimated transformer oil weight differs by more than a threshold amount from the characteristic transformer oil weight.

6. The method of claim 1, wherein fitting the transformer top-oil temperature model to the online measurements in the iterative optimization process to obtain the fitted characteristic values for the first and second parameters comprises iteratively adjusting the values of the first and second parameters in the transformer top-oil temperature model, to minimize the error between the top-oil temperature measurements and top-oil temperature estimates, as estimated from the transformer top-oil temperature model.

7. The method of claim 6, wherein iteratively adjusting the values of the first and second parameters comprises closing an error feedback loop through an optimization algorithm that adjusts the values of the first and second parameters, based on feeding back the error between the top-oil temperature measurements and top-oil temperature estimates as an input to the optimization algorithm.

8. The method of claim 7, wherein the optimization algorithm is a Nelder-Mead optimization algorithm.

9. The method of claim 1, wherein communicating the online measurements for the transformer comprises receiving electronic signaling directly or indirectly from the sensors sensing the ambient temperature in a vicinity of the transformer, the top-oil temperature of the oil in the transformer, and the winding current in at least one of a primary and a secondary winding of the transformer.

10. The method of claim 1, wherein generating the alarm signaling comprises outputting electronic signaling for transmission to a supervisory computer system associated with a transmission or distribution network in which the transformer is operating.

11. The method of claim 1, wherein generating the alarm signaling based on comparing the estimated transformer oil weight to the characteristic transformer oil weight comprises determining whether or not the estimated transformer oil weight differs by more than a threshold amount from the characteristic transformer oil weight for at least a defined number of evaluation cycles or for a duration in time that is longer than a defined evaluation window.

12. A system configured for monitoring for oil leakage from an oil-immersed electrical transformer, said system comprising:
at least one winding positioned within oil in the transformer;
a plurality of sensors comprising:
a top-oil temperature sensor positioned to measure a top-oil temperature of the oil within the transformer;
a temperature sensor positioned to measure an ambient temperature; and a current sensor positioned to measure a winding current of one or more of the at least one winding;

at least one communication interface that receives online measurements for the transformer from the plurality of sensors;

a supervisory computer system that interfaces with the at least one communication interface;

a processing circuit operatively associated with the at least one communication interface and configured to:

determine characteristic values from at least one of pre-configured factory values and collected historical measurements for first and second parameters of a transformer top-oil temperature model, wherein the first parameter represents the top-oil temperature rise over ambient temperature and the second parameter represents the oil time constant;

estimate, using at least the determined characteristic values for the first and second parameters with the transformer top-oil temperature model, a top-oil temperature;

compare the estimated top-oil temperature to the on-line measurements fit the transformer top-oil temperature model to the online measurements, in response to the comparison of the estimated top-oil temperature to the on-line measurements and in an iterative optimization process, to obtain fitted characteristic values for the first and second parameters;

estimate a transformer oil thermal capacitance as a function of the fitted characteristic values and correspondingly estimate a transformer oil weight as a function of the estimated transformer oil thermal capacitance;

generate alarm signaling based on comparing the estimated transformer oil weight to a characteristic transformer oil weight, the characteristic transformer oil weight being calculated from at least the characteristic values for the first and second parameters; and generate a maintenance diagnostic of the oil-immersed electrical transformer based on the generated alarm signaling, the maintenance diagnostic implemented by the oil-immersed electrical transformer to detect a loss of oil from the oil-immersed electrical transformer.

13. The system of claim 12, wherein the processing circuit is configured to determine the characteristic values based on being configured to perform at least one of:

initialize the characteristic values to the pre-configured factory values; and compute the characteristic values based on the collected historical measurements for the ambient temperature, the top-oil temperature and the winding current.

14. The system of claim 13, wherein the processing circuit is configured to compute the characteristic values by fitting the transformer top-oil temperature model to the historical measurements collected over a defined time window, to thereby obtain historical fitted characteristic values corresponding to the defined time window, which historical fitted characteristic values are stored as the characteristic values.

15. The system of claim 12, wherein the processing circuit is configured to repeat the fit, estimate and generate operations according to a defined leak-checking time interval.

16. The system of claim 12, wherein the processing circuit is configured to generate the alarm signaling based on comparing the estimated transformer oil weight to the characteristic transformer oil weight by determining whether or not the estimated transformer oil weight differs by more than a threshold amount from the characteristic transformer oil weight.

17. The system of claim 12, wherein the processing circuit is configured to carry out the iterative optimization process by iteratively adjusting the values of the first and second parameters in the transformer top-oil temperature model, to minimize the error between the top-oil temperature measurements and top-oil temperature estimates, as estimated from the transformer top-oil temperature model.

18. The system of claim 17, wherein the processing circuit is configured to iteratively adjust the values of the first and second parameters by closing an error feedback loop through an optimization algorithm that adjusts the values of the first and second parameters, based on feeding back the error between the top-oil temperature measurements and top-oil temperature estimates as an input to the optimization algorithm.

19. The system of claim 18, wherein the optimization algorithm is a Nelder-Mead optimization algorithm.

20. The system of claim 12, wherein the processing circuit is configured to obtain the online measurements for the transformer by receiving, via the at least one communication interface, electronic signaling directly or indirectly from the plurality of sensors, and wherein the plurality of sensors further includes an ambient temperature sensor that is positioned to sense an ambient temperature in a vicinity of the transformer, and wherein the current sensor measures the winding current in at least one of a primary and a secondary winding of the transformer.

21. The system of claim 12, wherein the processing circuit is configured to output electronic signaling from the at least one communication interface as the alarm signaling for transmission to the supervisory computer system.

22. The system of claim 12, wherein the processing circuit is configured to generate the alarm signaling based on comparing the estimated transformer oil weight to the characteristic transformer oil weight by determining whether or not the estimated transformer oil weight differs by more than a threshold amount from the characteristic transformer oil weight for at least a defined number of evaluation cycles or for a duration in time that is longer than a defined evaluation window.

* * * * *